US005233121A

United States Patent [19]

Modica

[11] Patent Number: 5,233,121

[45] Date of Patent: Aug. 3, 1993

[54] PROCESS FOR THE CATALYTIC ISOMERIZATION OF LIGHT HYDROCARBONS

[75] Inventor: Frank S. Modica, Naperville, Ill.

[73] Assignee: Amoco Corporation, Chicago, Ill.

[21] Appl. No.: 925,397

[22] Filed: Aug. 4, 1992

Related U.S. Application Data

[63] Continuation of Ser. No. 756,928, Sep. 9, 1991, abandoned, which is a continuation of Ser. No. 601,502, Oct. 23, 1990, abandoned.

[51] Int. Cl.[5] .......................... C07C 5/13; C10G 35/06

[52] U.S. Cl. .................................... 585/739; 585/751; 208/138; 208/135

[58] Field of Search ................ 585/739, 751; 208/138, 208/135

[56] References Cited

U.S. PATENT DOCUMENTS 5,082,988 1/1992 Holtermann ........................ 585/739

*Primary Examiner*—Anthony McFarlane
*Assistant Examiner*—Nhat D. Phan
*Attorney, Agent, or Firm*—Thomas A. Yassen; Richard A. Kretchmer; Frank J. Sroka

[57] ABSTRACT

The present invention relates to a process for isomerizing a light paraffinic naphtha feedstock having a boiling range from about 50° F. to about 210° F. and containing at least 85 weight percent aliphatic hydrocarbon having 6 carbon atoms or less. The process comprises contacting the feedstock at isomerization conditions with an isomerization catalyst comprising a zeolite beta component.

26 Claims, 6 Drawing Sheets

PROCESS FOR THE CATALYTIC ISOMERIZATION OF LIGHT HYDROCARBONS

This is a continuation of application Ser. No. 07/756,928, filed Sep. 9, 1991, now abandoned which in turn is a continuation of Ser. No. 07/601,502, filed Oct. 23, 1990, now abandoned.

BACKGROUND OF THE INVENTION

This invention relates to a process for the catalytic isomerization of light hydrocarbons. More particularly, this invention relates to a process for the catalytic isomerization of light hydrocarbons wherein the hydrocarbon stream contacts a catalyst comprising beta zeolite and a noble metal whereby the stream is upgraded to a product having an increased octane number.

Natural straight run gasoline (i.e., naphtha, or light naphtha) contains chiefly normal paraffins such as normal pentane and normal hexane, which have relatively low octane numbers. Representative clear octane numbers are set forth below in Table I.

TABLE I

| Paraffin | Octane Number Research Clear | Octane Number Motor Clear |
|---|---|---|
| n-Pentane | 61.7 | 61.9 |
| 2-Methylbutane | 92.3 | 90.3 |
| 2,2-Dimethylbutane | 91.8 | 93.4 |
| 2,3-Dimethylbutane | 103.5 | 94.3 |
| 2-Methylpentane | 73.4 | 73.5 |
| 3-Methylpentane | 74.5 | 74.3 |
| n-Hexane | 24.8 | 26.0 |

It is of great importance to convert these low octane components to their higher octane isomers in order to supply the present and future requirements for production of gasoline. Gasoline octane specifications will become more difficult to meet with the complete phase-out of lead from gasoline and future projected limitations on high octane aromatic content in gasoline. Accordingly, a considerable number of isomerization processes have been proposed for isomerization of hydrocarbons in the petroleum industry, however, there is still need for more effective isomerization processes.

The isomerization of n-paraffins is generally believed to be a first-order reversible reaction that proceeds through a dual functional mechanism over molecular sieve based catalysts. Although not to be construed as a limitation on the present invention, this mechanism can be summarized as follows:

1. n-alkane←,→n-alkene+$H_2$
2. n-alkene+$H^+$←,→n-$R^+$
3. n-$R^+$←,→i-$R^+$
4. i-$R^+$←,→i-alkene+$H^+$
5. i-alkene+$H_2$←,→i-alkane where $H^+$ is the acid site on the zeolite surface and $R^+$ is the adsorbed carbenium ion on the acid site.

Steps 1 and 5 are dehydrogenation reactions that take place on metal sites. Steps 2 and 4 involve chemisorption on acid sites to form carbenium ions. As long as sufficient metal sites are present and chemisorption on acid sites is facile, Step 3 is rate controlling, and Steps 1–2 and 4–5 are in near-equilibrium.

It is well recognized that the isomerization reaction is constrained by thermodynamic equilibrium between the normal paraffinic feedstock and the various isomers of this feedstock. Refiners target an economically desirable isomerate product by evaluating such parameters as the value of gasoline octane, yield, and facility cost, and develop or select processes that most economically meet their requirements. In order to ensure that refiners can maximize their degree of approach to the ideal equilibrium state of the reaction, refiners must consider the particular catalyst employed, the required feedstock preparation, and key process variables such as reaction temperature and pressure.

The isomerization reaction is particularly dependent on reaction temperature as is apparent in the case of light hydrocarbons such as hexane. If the isomerization reaction is carried out at high temperatures (over 600° F.), the doubly branched isomers are much less favored than singly branched isomers or n-hexane whereas at lower temperatures (below 400° F.), there is a rapid increase in the equilibrium concentration of the high octane isomer 2,2-dimethylbutane (J. A. Ridgway, Jr. and W. Schoen, ACS Symposium, Div. of Petroleum Chemistry, Boston, Apr. 5-10, 1959, A-5-A-11). FIG. 1 shows the composition-temperature equilibrium curves of the vapor phase hexane isomers as determined by Ridgway and Schoen. The curves show the more favorable equilibrium at lower reaction temperatures. However, like most catalytic reactions, the rate of reaction decreases as the reaction temperature is decreased, and the reaction will not closely approach equilibrium at low operating temperatures. At high reaction temperatures, hydrocracking increases rapidly, increasing the yield of undesirable lighter hydrocarbons at the expense of liquid products. High reaction temperatures can also increase the rate of carbon laydown (coking) on the catalyst resulting in catalyst deactivation. Thus, there is an optimum temperature range at which the isomerization reaction just begins to approach equilibrium while still minimizing the undesirable side reactions. For most molecular sieve-based isomerization catalysts, the optimum temperature lies in the range from 300°–700° F., with a preferred range from 450°–500° F. This optimum temperature, in general, is different for different catalysts with different activities and selectivities. A catalyst which operates at a lower optimum temperature is also able to take advantage of the more favorable equilibrium and lower rate of hydrocracking and coking at lower temperatures.

Feedstock composition is a key determinant as to catalyst selection and development and facility design. Catalyst contact with known isomerization poisons such as sulfur, nitrogen, and water can result in irreversible catalyst deactivation and poor product yields. Catalyst contact with heavy components with 7 or more carbon atoms or cyclics of 6 carbon atoms or more can result in adverse competitive reactions that either result in a lower octane product or in interference with the isomerization reactions by adsorption on the catalyst. For example, the presence of benzene in the feedstock results in strong adsorption on the catalyst acid sites which interferes with normal pentane and normal hexane isomerization. The benzene itself is saturated to form cyclohexane which has a substantially lower octane. The presence of heavy components with 7 or more carbon atoms also strongly inhibits the normal pentane and normal hexane isomerization reaction and increases reaction space velocity in the process of being substantially hydrocracked to lower value propane and butane products. While essentially inert to the isomerization reaction, the processing of lighter hydrocarbons of 4 carbon atoms or less in an isomerization unit adversely affects isomerization yields of normal pentane and normal hexane by increasing reactor space velocity (WHSV).

Lower reaction pressures in an isomerization process are beneficial and result in a higher rate of reaction and a closer approach to thermodynamic isomerization equilibrium. Lower pressure operations also result in construction savings (i.e., lower equipment design pressures, etc.) and reduced operating costs such as compressor horsepower. However, extremely low reaction pressures can increase catalyst coking and result in catalyst deactivation. Effective isomerization processes and catalysts must address and optimize these parameters.

Most isomerization processes are categorized as either low temperature isomerization or high temperature isomerization. Low temperature isomerization processes typically feature a highly chlorided platinum on alumina catalyst which provides high catalyst activity and permits operation at lower temperatures. Adversely, these chlorided catalyst processes require higher investment costs, are more difficult to operate, and are substantially more vulnerable to contaminants and catalyst deactivation.

High temperature isomerization process catalysts typically contain platinum or other noble metal on a molecular sieve base which does not provide the level of catalyst activity of the low temperature catalyst. However, the high temperature catalyst is much more resistant to contaminants such as sulfur and water and the processing facilities are less expensive to build. Examples of catalysts used in this type of process are disclosed in U.S. Pat. No. 3,236,903 where the catalyst is a zeolite molecular sieve containing a catalytically active metal such as rhodium, U.S. Pat. Nos. 3,236,761 and 3,236,762 where the catalyst is a Y-type crystalline zeolite containing an elemental metal of Group VIII of the Periodic Table, U.S. Pat. Nos. 3,527,835 and 3,299,153 where the catalyst is a synthetic mordenite containing highly-dispersed platinum or palladium contacted with hydrocarbon in the presence of hydrogen, and U.S. Pat. No. 3,354,077 where the catalyst is a stabilized Y-sieve hydrogen zeolite composition. A particularly common catalyst in commercial practice today is the synthetic mordenite catalyst containing a highly-dispersed platinum or palladium.

Use of zeolite beta as a catalyst component has been the subject of several catalyst synthesis patents. U.S. Pat. Nos. 4,642,226, 4,554,145, 4,683,214, and 4,615,997 are all directed towards methods for preparing catalysts which include some percentage of zeolite beta.

U.S. Pat. No. 4,518,485 discloses the use of zeolite beta as a catalyst component in a lubricating oil dewaxing process. Lube oil stock is hydrotreated over a zeolite beta catalyst for the purpose of isomerizing heavy straight-chained paraffins into branched, lower pour-point isomers and hydrocracking other heavy, high viscosity lube oil components into lower viscosity components.

U.S. Pat. Nos. 4,753,720 and 4,784,745 disclose the use of zeolite beta as a catalyst component for octane improvement of refinery produced olefinic gasoline. The process treats the cracked olefinic naphtha streams produced at a Fluid Catalytic Cracking Unit or a Coking Unit at low reaction pressures and in the absence of hydrogen so as to improve the octane of the streams.

U.S. Pat. No. 4,647,368 discloses use of zeolite beta as a catalyst component for processing full range $C_4$ to $C_{10}$ naphtha. The patent discloses that the butane component is isomerized, the pentane and hexane component is isomerized, while the heptane and heavier material component is partially hydrocracked. While the process can eliminate prefractionation steps in converting the wide range of feed components into intermediate or finished products, the process generally results in lower total gasoline octane production from less effective isomerization of the pentane and hexane component, lower gasoline yield from hydrocracking gasoline boiling range material into butane and lower boiling point components, lower refinery hydrogen production from a reduction in reformer feedstock volume to light ends, and require more costly capital due to the necessity of a very large, full-range naphtha processing facility.

It is an object of the present invention to provide a light straight-run isomerization process that involves the use of a catalyst that resists catalyst deactivation due to feedstock contaminants and poisons.

It is another object of the present invention to provide an isomerization process that permits operation at relatively lower temperatures.

It is yet another object of the present invention to provide a process that increases octane upgrade without a decrease in gasoline yield, decrease in refinery hydrogen production, or the installation of higher cost processing facilities.

SUMMARY OF THE INVENTION

The above objects can be attained by providing a process for the isomerization of a light paraffinic hydrocarbon feedstock, the feedstock consisting essentially of a stream having a boiling range of from about 50° F. to about 210° F. and containing at least 85 weight percent aliphatic hydrocarbon having 6 carbon atoms or less. The process comprises contacting the feedstock at isomerization conditions with an isomerization catalyst comprising a zeolite beta component.

The process of the present invention has significant advantages over comparative processes. In contradistinction to U.S. Pat. No. 4,647,368 which teaches the isomerization and hydrocracking of full range naphtha, the present invention utilizes an optimized feedstock that, when processed with the zeolite beta catalyst and under the process conditions of the present isomerization process, provides unexpectedly superior results.

The present invention provides for a feedstock with less undesirable $C_7$ and heavier and cyclic components. The lower concentration of these undesirable components results in lower catalyst deactivation rates and extended catalyst life which reduces catalyst costs. Moreover, the absence of high concentrations of these undesirable components beneficially results in higher conversion of the pentane and hexane aliphatics to their isomers and a higher octane product. The absence of these undesirable components from the isomerization feedstock permits more selective isomerization without the substantial penalties associated with hydrocracking of the undesirable material. These penalties include a reduction in gasoline yield and an increase in the yield of low value components such as propane and butane and a reduction in the yield of these $C_7$ and heavier and cyclic components available for reforming into high-octane gasoline blending components and hydrogen. An attendant advantage of the present invention is that the $C_7$ and heavier and cyclic components are not processed in the isomerization unit and are only generally processed in a reformer. This reduces the facility requirements from those used in U.S. Pat. No. 4,647,368 by elimination of duplicate capacity required to process $C_7$ and heavier and cyclic components at an isomerization/hydrocracker operation and again at a reformer. By optimizing the feedstock to limit butane concentration, the process limits the costly consumption of reactor space velocity by a component that is only marginally upgraded.

A more detailed explanation is provided in the following description and appended claims taken in conjunction with the accompanying figures.

DETAILED DESCRIPTION

Figure 1:
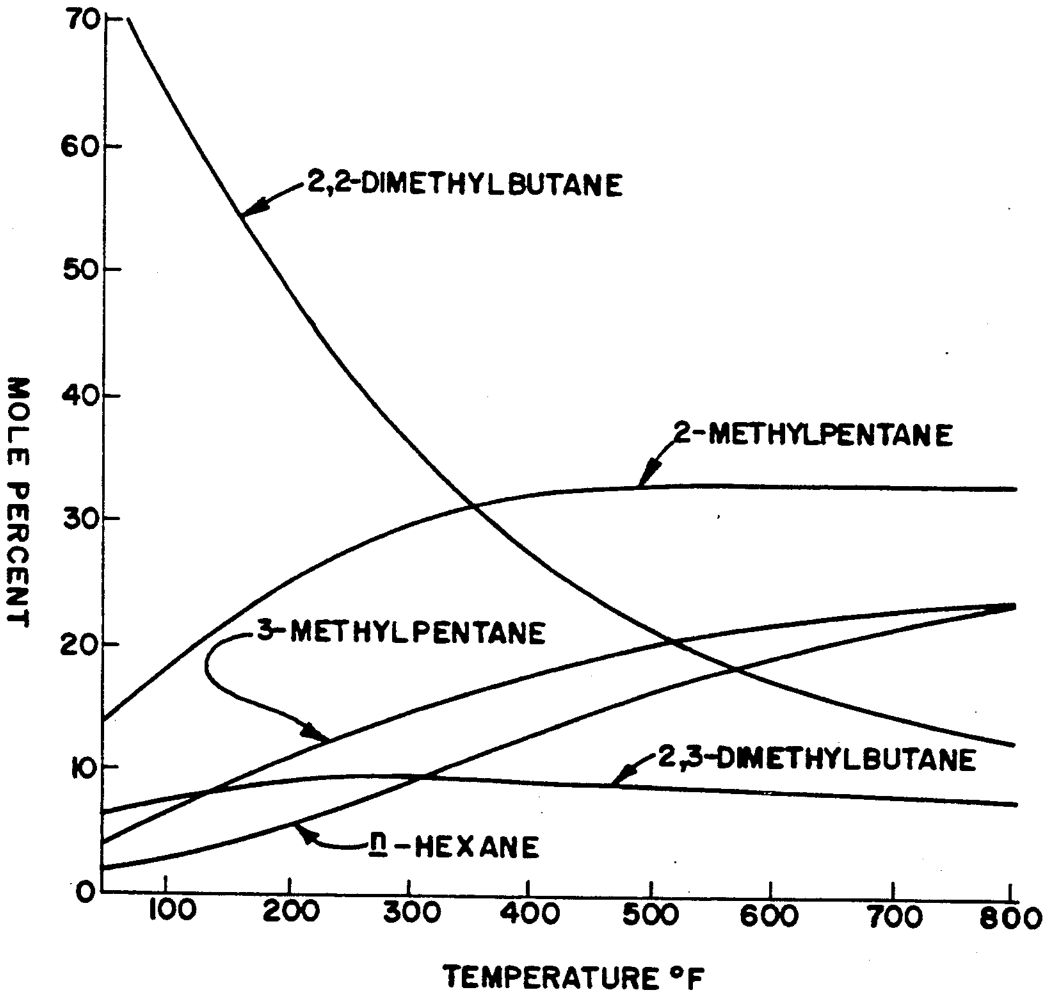
FIG. 1 is a graph describing the vapor phase isomer equilibrium for hexane at various temperatures.

The light paraffinic hydrocarbon feedstock processed in the present isomerization process can comprise light straight run or light virgin naphtha which is generally derived directly from a crude distillation unit. The feedstock may also include debutanized natural gasoline (DNG) which can be obtained as an intermediate feedstock, not necessarily fractionated from crude within a refinery. The feedstock can also include paraffinic pentane and hexane components generated from other refinery operations such as, but not limited to, a catalytic reformer. The feedstock used in accordance with the present invention possesses a boiling point range of from about 50° F. to about 210° F. at atmospheric pressure and contains substantially aliphatic hydrocarbons having 5 to 6 carbon atoms. The invention feedstock concentration of aliphatic hydrocarbons having 5 to 6 carbon atoms is at least about 85% by weight, preferably at least 91% by weight, and most preferably at least 94% by weight.

Feed components having 4 carbons atoms or less will generally pass through the process with little beneficial conversion and should be minimized. Some conversion from normal to isobutane can occur, however, the adverse effects of reduction of reactor space velocity and resultant loss of approach towards reaction thermodynamic equilibrium for the normal pentane and normal hexane streams will generally outweigh the benefits of this normal conversion. In addition, the processing of hydrocarbons having 4 carbon atoms or less will consume additional energy and facility capacity. Preferably, the butane concentration of the isomerization reactor feedstock should be minimized at less than about 5% by weight, preferably less than about 3% by weight, and more preferably less than about 2% by weight.

Components having 7 carbon atoms or more adversely affect the isomerization reaction and should be minimized. Components having 7 carbon atoms or more generally inhibit the normal pentane and normal hexane isomerization reaction, thereby resulting in an isomerate product having a lower octane number. In addition, as much as 70% by weight of the $C_7$ and heavier material can be deleteriously hydrocracked to low value propane and butane. The butane production can be especially costly during the summer months when lower gasoline volatility specifications mandate lower concentrations of butane in gasoline.

Cyclic components also adversely affect the isomerization reaction and should be minimized. The presence of cyclics such as benzene and methylcyclopentane strongly inhibit the isomerization reaction to high octane isomers by the adsorption of these components on the catalyst acid sites. Cyclics also create a larger isomerization reaction exotherm through aromatic hydrogenation, which increases the average reaction temperature resulting in undesirably lower selectivity to higher octane isomers. Aromatics such as benzene not only interfere with the isomerization reaction, but are downgraded to lower octane gasoline blending components such as cyclohexane. Therefore, the cyclic hydrocarbon components plus all other non-cyclic hydrocarbon components having 7 carbon atoms or more are preferably limited in the feedstock to less than about 10% by weight, more preferably to less than about 5% by weight and, most preferably, to less than about 3% by weight.

Olefinic components adversely affect the isomerization reaction and should be minimized. High concentrations of olefinic components increase carbon laydown (coking) resulting in catalyst deactivation. Moreover, olefins are generally hydrogenated in the isomerization process. This olefinic hydrogenation reaction is exothermic and unfavorably increases the isomerization reaction temperature. Preferably, the olefin concentration of the isomerization reactor feedstock should be minimized at less than about 10% by weight, preferably less than about 8% by weight and, more preferably, less than about 5% by weight.

Catalyst poisons such as nitrogen, sulfur, and water must be kept at a minimum in order to prevent catalyst deactivation. Many operating facilities are equipped with hydrotreater sections on the isomerization facility to reduce nitrogen and sulfur contaminant levels in the feedstock prior to introduction into the isomerization reactors. Generally, isomerization reactor feed should contain less than about 3 ppm by weight of nitrogen and less than 3 ppm by weight of sulfur, preferably at less than 2 ppm by weight of nitrogen and less than 2 ppm by weight of sulfur, and more preferably less than 1 ppm by weight of nitrogen and less than 1 ppm by weight of sulfur for best results. Regenerative molecular sieve dryers can be provided to minimize water content in isomerization reactor feed. Isomerization reactor feed should contain less than 250 ppm by weight water, preferably less than 100 ppm by weight water and, more preferably, less than 50 ppm by weight paper for best results.

The isomerization catalyst used in the present light paraffin isomerization process comprises a support component containing beta zeolite and a hydrogenating component. Zeolite beta is a known zeolite which is described in U.S. Pat. Nos. 3,308,069 and Re. 28,341 the teachings of which are incorporated by reference, to which reference is made for further details as to this zeolite, its preparation, and properties. The composition of zeolite beta in its as-synthesized form (anhydrous basis) is as follows:

$$[XNa(1.0\pm0.1-X)TEA]AlO_{2vs}\ YSiO_2$$

wherein X is less than 1, preferably less than 0.75; TEA represents the tetraethylammonium ion; and Y is greater than 5 but less than 100. In the assynthesized form, water of hydration may also be present.

The sodium is derived from the synthesis mixture used to prepare the zeolite. The synthesis mixture contains a mixture of the oxides (or the materials whose chemical compositions can be completely represented as mixtures of the oxides), $Na_2O$, $Al_2O_3$, $[(C_2H_5)_4N]_2O$, $SiO_2$, and $H_2O$. The mixture is held at a temperature of from about 167° F. to about 392° F. until crystallization occurs. The composition of the reaction mixture expressed in terms of mole ratios preferably falls within the following ranges:

$SiO_2/Al_2O_3$—1:1 to 200:1

$Na_2O$/tetraethylammonium hydroxide (TEAOH)—0.0 to 1.0

TEAOH/$SiO_2$—0.1 to 1.0

$H_2O$/TEAOH—20 to 75.

The product which crystallizes from the hot reaction mixture is separated by centrifuging or filtration, washed with water, and dried. The material obtained may be calcined by heating in air or an inert atmosphere at a temperature usually within the range of about 392° F. to about 1652° F. The calcination degrades the tetraethylammonium ions to hydrogen ions and removes the water. The formula of the zeolite is then:

$$[XNa(1.0\pm0.1-X)H]AlO_2YSiO_2$$

where X and Y have the values ascribed to them above. The degree of hydration is here assumed to be zero, following the calcination.

If this H-form zeolite is subjected to base exchange, the sodium may be replaced by another cation to give a zeolite of the formula (anhydrous basis):

$$[XM/n(1.0\pm0.1-X)H]AlO_2YSiO_2$$

where X and Y have the values ascribed to them above, and n is the valence of the metal M which may be any metal but is preferably a metal of Groups IA, IIA, or IIIA of the Periodic Table or a transition metal (the Periodic Table referred to in this specification is the table approved by IUPAC, and the U.S. National Bureau of Standards).

The as-synthesized sodium form of the zeolite may be subjected to base exchange directly without intermediate calcination to give a material of the formula (anhydrous basis):

$$[X\ M/n(1\pm0.1-X)TEA]AlO_2YSiO_2$$

where X, Y, n, and M are described above. This form of the zeolite may then be converted partly to the hydrogen form by calcination, e.g. at 392° F. to about 1652° F. The completely hydrogen form may be made by ammonium exchange followed by calcination in air or an inert atmosphere such as nitrogen. Base exchange may be carried out in the manner disclosed in U.S. Pat. Nos. 3,308,069 and U.S. Pat. No. Re. 28,341.

Because tetraethylammonium hydroxide is used in its preparation, zeolite beta may contain occluded tetraethylammonium ions (e.g., as the hydroxide or silicate) within its pores in addition to that required by electroneutrality and indicated in the calculated formulae given in this specification. The formulae are calculated using one equivalent of cation per Al atom in tetrahedral coordination in the crystal lattice.

Zeolite beta, in addition to possessing a composition as defined above, may also be characterized by its X-ray diffraction data which are set out in U.S. Pat. No. 3,308,069 and U.S. Pat. No. Re. 28,341. The significant d values (Angstroms, radiation: K alpha doublet of copper, Geiger counter spectrometer) are as shown in Table II below:

TABLE II

| d Values of Reflections in Zeolite Beta |
|---|
| 11.40 + 0.2 |
| 7.40 + 0.2 |
| 6.70 + 0.2 |
| 4.25 + 0.1 |
| 3.97 + 0.1 |
| 3.00 + 0.1 |
| 2.20 + 0.1 |

It is clear that the zeolite beta catalyst of the present invention displays improved activity compared to the isomerization catalysts of the prior art when employed with a feedstock having the characteristics stipulated by the instant invention. The source of the improved activity is not well understood but is generally believed to be related to an improved pore structure and the presence of stronger acid sites than found in comparative catalysts. Like mordenite, zeolite beta contains large pores bounded by rings of twelve oxygen atoms. However, mordenite has a one-dimensional channel system (i.e., the microporous structure is made up of channels which are parallel with one another and without interconnections large enough for reactant molecules to pass through). Zeolite beta has a two-dimensional channel system (i.e., the microporous structure is made up of two sets of channels with one set of channels perpendicular to and intersecting the other set). The spaces where the channels intersect have a larger diameter than the channels themselves. Furthermore, the pores in zeolite beta are more nearly cylindrical, while the pores in mordenite are somewhat oval in shape. As a result of these differences in pore geometry, reactant diffusion in mordenite is more strongly limited. This effect can be measured by a variety of techniques. One of these techniques is the "spaciousness index" which is described in Applied Catalysts, 27, published by Elsevier Science Publishers B. V., Amsterdam, Netherlands, on pages 207 through 210 and is hereby incorporated by reference.

The spaciousness index measures the diffusional hindrance of a pore structure. A higher spaciousness index indicates a larger or less diffusionally hindered pore structure. The reported spaciousness index of zeolite beta is about 19 which is close to the value for zeolite Y, a zeolite known to have a large open pore structure. The reported spaciousness index for mordenite is about 8, which is closer to the value reported for ZSM-5, an intermediate pore zeolite with pores made up of only ten-membered rings. The lower diffusional resistance to passage of reactant and product molecules of the zeolite beta catalyst used in the process of the present invention can contribute to the higher activity.

The strength of the acid sites in zeolite beta may also be greater than other isomerization catalysts such as those using a mordenite support component. Since isomerization is an acid-catalyzed reaction, this increase in acid strength can increase the rate of reaction on each individual acid site, increasing the overall rate of reaction.

The zeolite beta component of the catalyst useful in the present isomerization process, can be synthesized having a range of silica/alumina ratios. Generally, as the silica/alumina ratio decreases, the number of acid sites increase, but the acid strength per site decreases. Thus, it is important to optimize the silica/alumina ratio in a manner which maximizes catalyst activity and selectivity. The preferred forms of zeolite beta for use in the present light paraffin isomerization process are the forms having a silica/alumina ratio of from about 4:1 to about 100:1, preferably from about 6:1 to about 50:1, and more preferably from about 8:1 to about 30:1 for best results.

The zeolite beta component of the catalyst useful in the present isomerization process, in order to be effective, must be employed in its acidic form. This is accomplished by ion-exchange of the alkali metals normally found in the as-synthesized zeolite. This ion-exchange can be accomplished in several ways using such exchanging compounds as ammonium nitrate, ammonium sulfate, dilute hydrochloric acid, and acetic acid. Residual alkali metal content should be less than 1% by weight, preferably less than 0.5% by weight, and more preferably less than 0.2% by weight for best results.

The support component of the catalyst useful in the present invention can comprise the zeolite beta component and a binder component. The binder component can be mixed with the zeolite beta powder prior to particle formation in order to improve the crush strength of the particles. The binder component can be alumina, silica, silica-alumina, clay, diatomaceous earth or other binders known in the art. Since the binder material is essentially inert to the isomerization reaction, the amount of binder used should be enough to impart the desired crush strength without unnecessarily diluting the zeolite beta fraction. The catalyst of the present isomerization process comprises from about 10% to about 99% zeolite beta by weight, preferably from about 40% to about 99% zeolite beta by weight, and most preferably from about 70% to about 80% zeolite beta by weight.

The hydrogenation metal is incorporated into the support component of the catalyst of the present isomerization process to catalyze the hydrogenation-dehydrogenation step of the isomerization reaction. The hydrogenation metal should be a metal component selected from the Group VIII elements of the Periodic Table (IUPAC), preferably platinum or palladium, and most preferably platinum. The amount of metal employed will depend on the particular metal employed and should be sufficient to catalyze the hydrogenation-dehydrogenation reaction such that this step is essentially in thermodynamic equilibrium and not rate-limiting.

The hydrogenation metal can be added by ion-exchange, impregnation, or other means known in the art. It is important however, that the metal is distributed throughout the catalyst particle. One method of incorporation is ion-exchange using a cationic metal complex and a large excess of a competing ion as described by Benesi in U.S. Pat. No. 3,527,835 which is hereby incorporated by reference. The competing ions are rapidly adsorbed by the catalyst surface and slowly displaced by the metal complex, allowing diffusion of the metal into the catalyst particle. The catalyst of the isomerization process of the present invention should comprise from about 0.01% to about 5% by weight of hydrogenation metal, preferably from about 0.1% to about 1% by weight of hydrogenation metal, and more preferably from about 0.2% to about 0.8% by weight of hydrogenation metal.

The isomerization process of the present invention can begin with initial feed preparation steps. The feedstock can be subjected to a feedstock drying step. In this operation, all or part of the feedstock can be dried in a facility such as a regenerative molecular sieve dryer in order to extend catalyst life. The hydrogen that is introduced or recycled back to the process may also be dried. The catalyst of the present invention is especially resistant to water deactivation and can tolerate water concentrations of as high as 250 ppm by weight. Preferably the isomerization reactor feedstock water content is maintained below about 100 ppm by weight, and more preferably below about 50 ppm by weight. Drying facilities, while essential in the low temperature processes of the prior art, are usually not necessary in the present process.

The feedstock can be subjected to normal paraffin concentration processes such as those involving the use of a molecular sieve adsorbent having a pore diameter suitable for separation of isomers from normal paraffins. Concentration devices of this type can be applied to the feedstock or to the isomerate product steam and utilized to increase the conversion of normal paraffins to isoparaffins.

The feedstock is generally subjected to a feedstock hydrogenation and desulfurization step which is operated to remove the catalyst poisons described above prior to introduction to the isomerization reactors. A catalyst comprising a hydrogenation-dehydrogenation component on a porous inorganic oxide support such as alumina, silica, or alumina-silica is generally used. Suitable hydrogenation components are base metals of groups VIA or VIIIA of the Periodic Table (IUPAC) and usually will be a base metal or a combination of base metals, although noble metals such as platinum and palladium may be used. Examples of suitable base metals include molybdenum, nickel, cobalt, and tungsten and combinations of base metals such as nickel-tungsten, cobalt-molybdenum, and nickel-tungsten-molybdenum. Hydrotreating process conditions comprise temperatures of from about 500° F. to about 800° F., pressures of from about 400 psig to about 1000 psig, and a hydrogen circulation rate of from 300 SCF/BbI to about 600 SCF/BbI. A separation device such as a stripping tower can be employed to facilitate removal of the catalyst poison components (e.g., nitrogen and sulfur) from the hydrotreater effluent.

The feedstock can then be subjected to isomerization over the zeolite beta-containing catalyst of the present invention process. The isomerization process reaction section of the present invention operates at elevated temperatures and pressures and in the presence of hydrogen. Reaction temperatures range from about 300° F. to about 700° F., preferably from about 400° F. to about 600° F., and most preferably from about 450° F. to about 500° F. for best results. Reaction pressures range from about 50 psig to about 800 psig, preferably from about 100 psig to about 600 psig, more preferably from about 200 psig to about 400 psig, and most preferably from about 250 psig to about 350 psig. Space velocities (WHSV) range from about 0.1 $hr^{-1}$ to about 10.0 $hr^{-1}$, preferably from about 0.5 $hr^{-1}$ to about 5.0 $hr^{-1}$, and most preferably from about 1.0 $hr^{-1}$ to about 3.0 $hr^{-1}$ for best results. Hydrogen circulation rates are commonly in the range of from about 200 SCF/BbI of isomerization reactor feedstock to about 2000 SCF/BbI, and most preferably from about 500 SCF/BbI of isomerization reactor feedstock to about 1500 SCF/BbI. Hydrogen partial pressure will generally comprise from about 40% to about 80% of the isomerization reaction pressure and is provided to reduce catalyst deactivation from coking. Hydrogen can be supplied in pure form or as a by-product of other refinery or petrochemical processes such as a refinery catalytic reforming unit.

Figure 2:
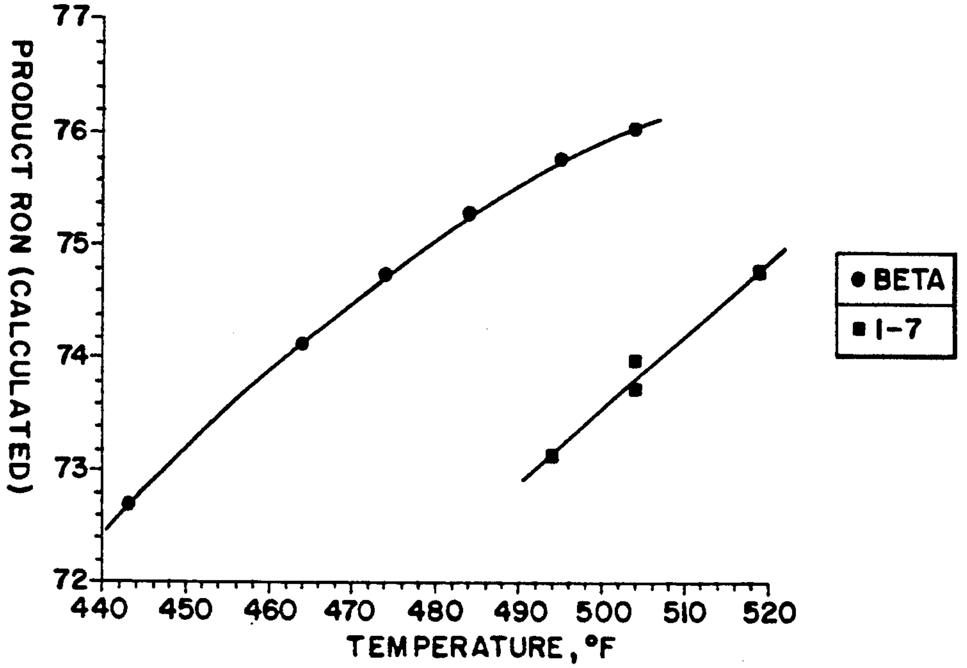
FIG. 2 is a graph illustrating a comparison of research octane and reaction temperature for the isomerization catalyst of the present invention and a commercially available catalyst (UOP 1-7)

The zeolite beta isomerization catalyst used in the present invention process is much more active than comparative resilient high temperature molecular sieve catalysts. FIG. 2 illustrates a comparison of research octane and reaction temperature for the isomerization catalyst of the present invention and a commercially available catalyst (UOP 1-7). The figure indicates that an isomerate product with the same research octane can be obtained at about a 40° F. to about 50° F. lower reaction temperature.

Figure 3:
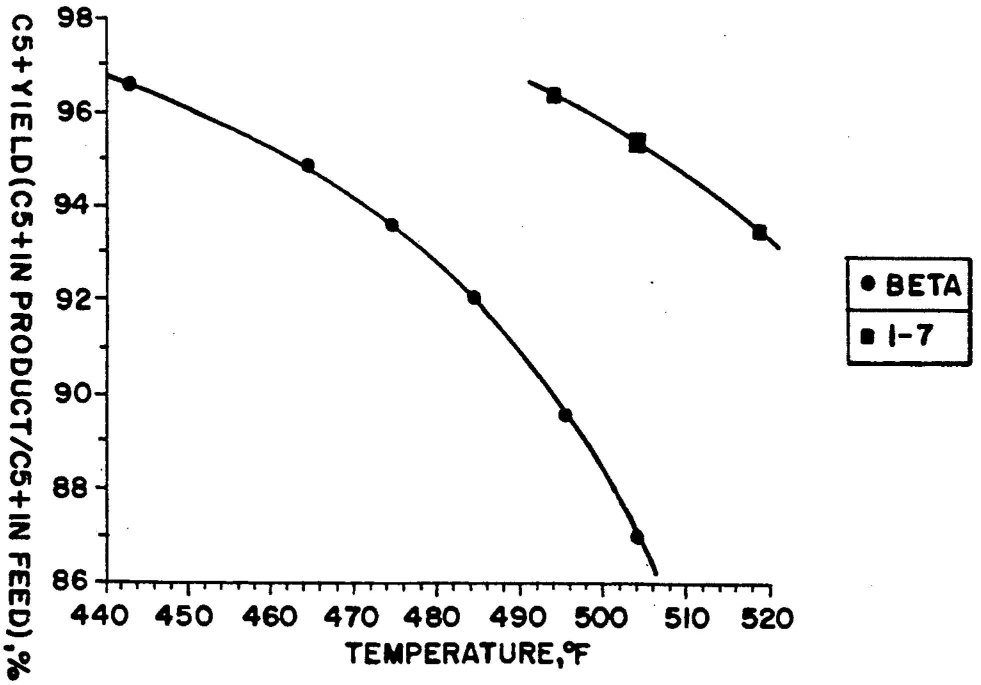
FIG. 3 is a graph illustrating a comparison of $C_5+$ material in the isomerate product as a percentage by weight of the $C_5+$ material in the reactor feed and reaction temperature for the isomerization catalyst of the present invention and a commercially available catalyst (UOP 1-7)

While activity for improving octane is increased, activity for cracking is also increased, resulting in a lower $C_5+$ (hydrocarbon with 5 or more carbon atoms) yield by weight. FIG. 3 illustrates that the $C_5+$ material in the isomerate product as a percentage by weight to the $C_5+$ material in the reactor feed is reduced by about 7% at the same temperature of about 500° F. However, by adjusting the reaction temperature of the present process to maintain the same $C_5+$ yield by weight for both isomerization processes, the isomerization product research octane is comparable for both processes.

Figure 4:
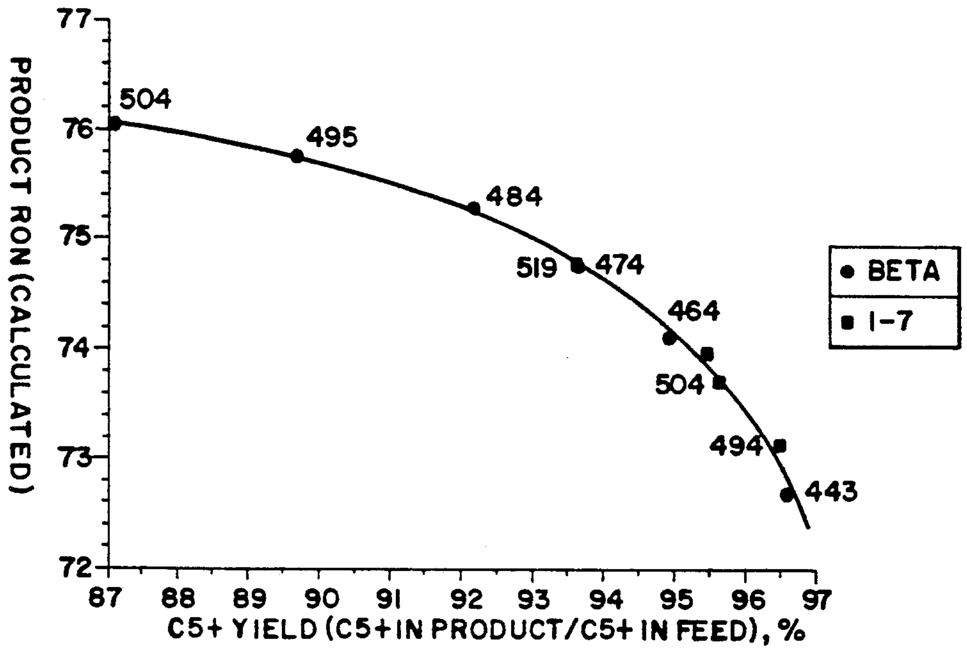
FIG. 4 is a graph illustrating the relationship between isomerate research octane and $C_5+$ material in the isomerate product as a percentage by weight of the $C_5+$ material in the reactor feed for the isomerization catalyst of the present invention and a commercially available catalyst (UOP 1-7)

FIG. 4 illustrates that the relationship between isomerate research octane and $C_5+$ material in the isomerate product as a percentage by weight of the $C_5+$ material in the reactor feed is comparable. The net result is that the zeolite beta catalytic process of the present invention produces an isomerate product with an equivalent product Research Octane Number (RON) and $C_5+$ yield at about a 40° F. to about a 50° F. lower temperature than a comparative commercial catalytic process.

Figure 5:
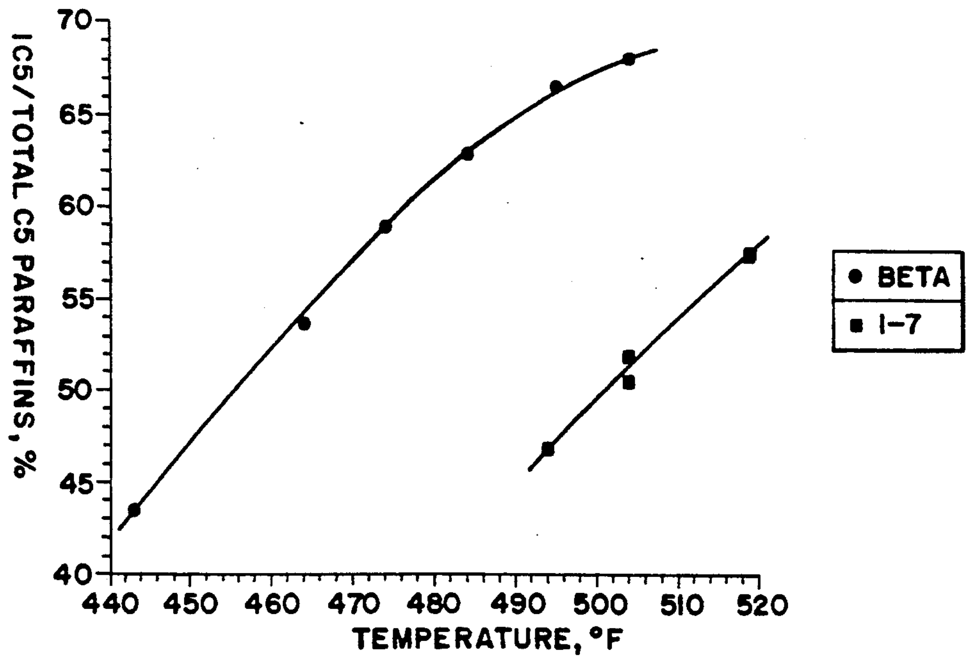
FIG. 5 is a graph illustrating a comparison of isopentane production as a percentage of $C_5$ paraffins in the isomerate product by weight and reaction temperature for the isomerization catalyst of the present invention and a commercially available catalyst (UOP 1-7)
Figure 6:
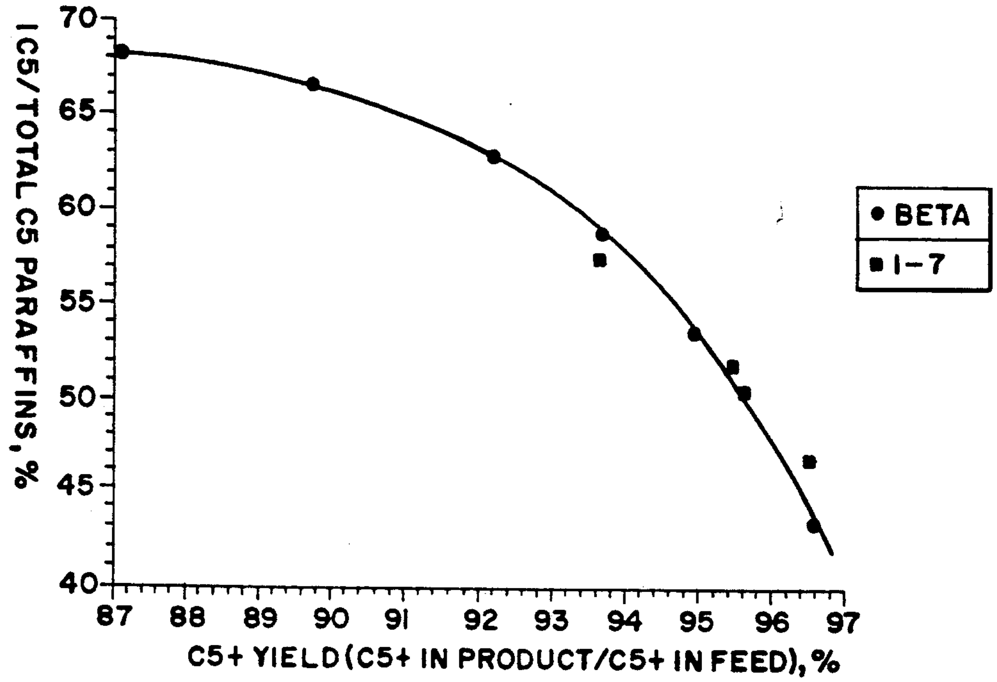
FIG. 6 is a graph illustrating the relationship between isopentane production as a percentage of $C_5$ paraffins in the isomerate product by weight and $C_5+$ material in the isomerate product as a percentage by weight of the $C_5+$ material in the reactor feed for the isomerization catalyst of the present invention and a commercially available catalyst (UOP 1-7).

The isomerate product yield structure/RON relationship of pentane alone for both the present invention and the comparative process closely mirrors the yield structure/RON relationship for the entire isomerate streams. Activity for isopentane conversion is much higher in the present invention, where a zeolite beta-containing catalyst is employed, than in the comparative process. Equivalent conversion to isopentane is obtained at about a 40° F. lower temperature than for the comparative catalyst (see FIG. 5). At constant $C_5+$ yields by weight as a percentage of $C_5+$ material in the reactor feed, FIG. 6 illustrates that the selectivity for conversion to isopentane is about the same as for the comparative process.

The isomerate product yield structure and the attendant RON relationship for hexane similarly results in equivalent isomerization results at lower reaction temperatures. The isomerization of normal hexane occurs in two steps:

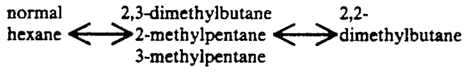

The first step is the isomerization of normal hexane into 2,3-dimethylbutane, 2-methylpentane, and 3-methylpentane. These three components are rapidly interconverted and are in near equilibrium with each other. Formation of 2,2-dimethylbutane occurs in a second step. There is no direct route from normal hexane to 2,2-dimethylbutane.

Figure 7:
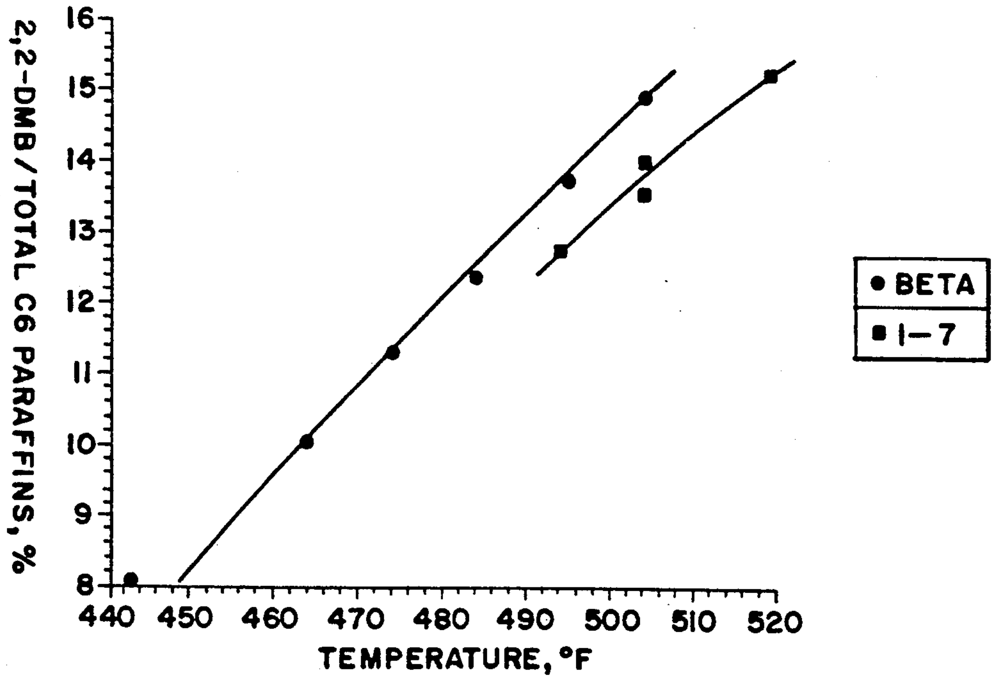
FIG. 7 is a graph illustrating a comparison of 2,2-dimethylbutane production as a percentage of $C_6$ paraffins in the isomerate product by weight and $C_5+$ material in the isomerate product as a percentage by weight of the $C_5+$ material in the reactor feed for the isomerization catalyst of the present invention and a commercially available catalyst (UOP 1-7)
Figure 8:
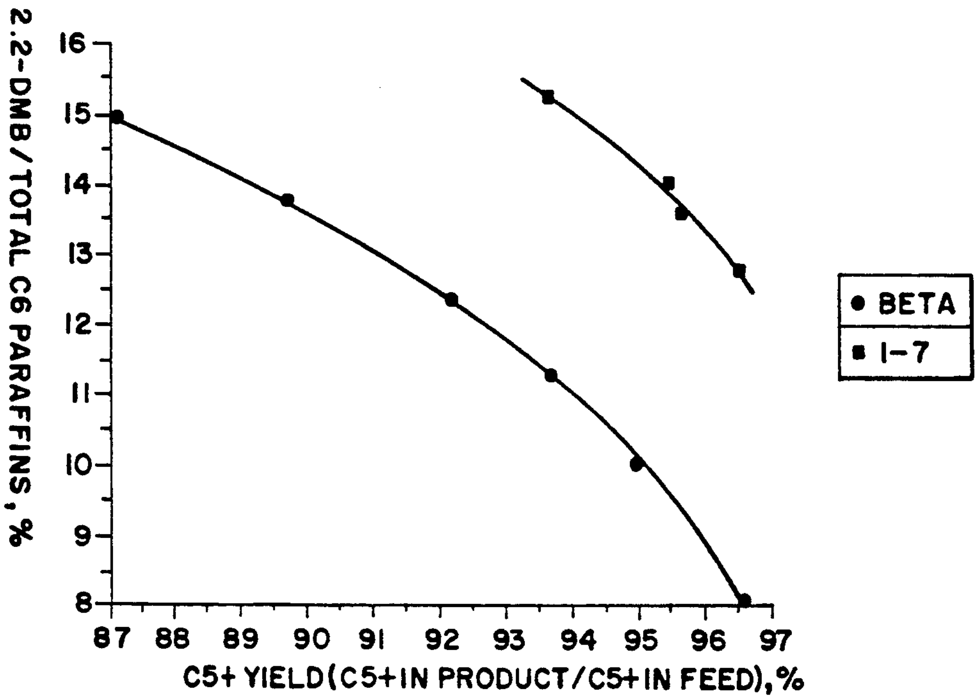
FIG. 8 is a graph illustrating a comparison of 2,2-dimethylbutane production as a percentage of $C_6$ paraffins in the isomerate product by weight and $C_5+$ material in the isomerate product as a percentage by weight of the $C_5+$ material in the reactor feed for the isomerization catalyst of the present invention and a commercially available catalyst (UOP 1-7)
Figure 9:
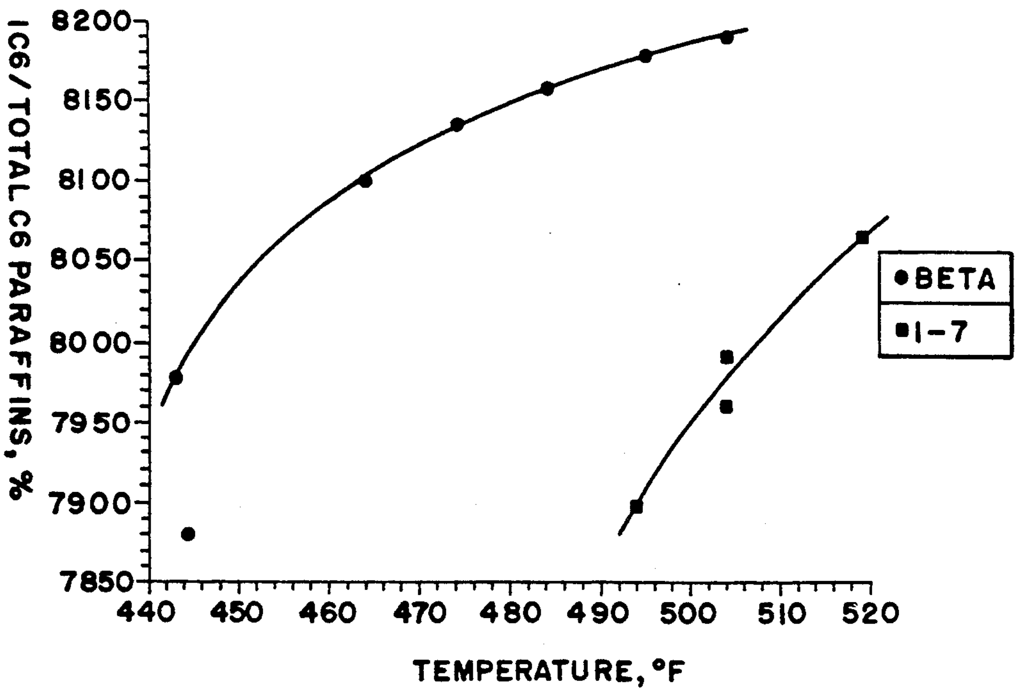
FIG. 9 is a graph illustrating a comparison of total isohexane production as a percentage of total $C_6$ paraffins in the isomerate product by weight and reaction temperature for the isomerization catalyst of the present invention and a commercially available catalyst (UOP 1-7)
Figure 10:
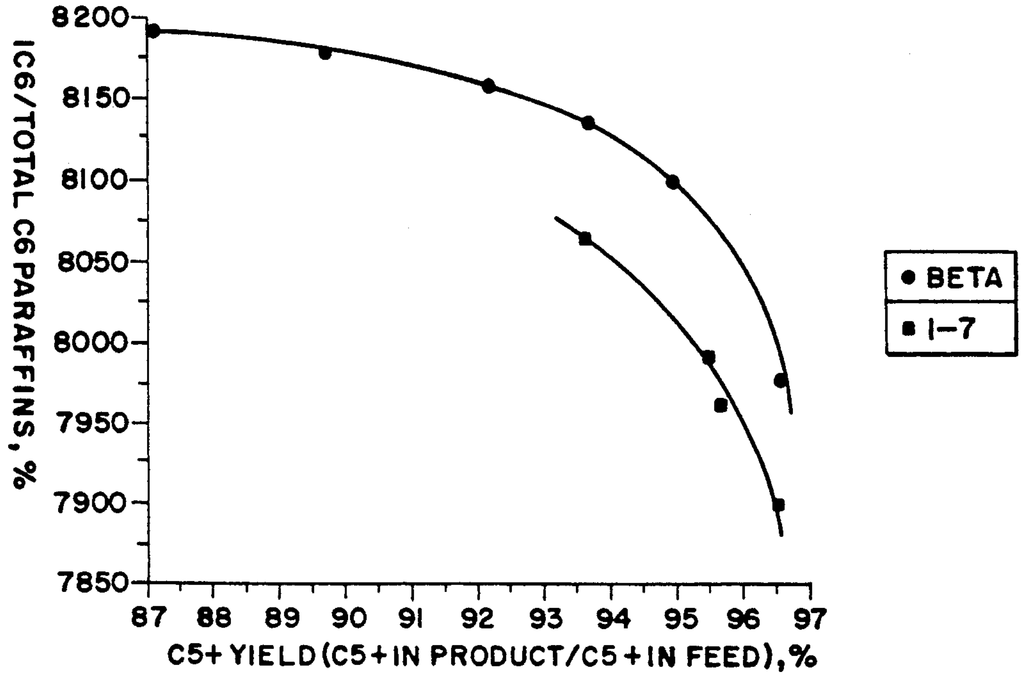
FIG. 10 is a graph illustrating a comparison of total isohexane production as a percentage of total $C_6$ paraffins in the isomerate product by weight and $C_5+$ material in the isomerate product as a percentage by weight of the $C_5+$ material in the reactor feed for the isomerization catalyst of the present invention and a commercially available catalyst (UOP 1-7)

Activity for the production of 2,2-dimethylbutane is only slightly higher than that observed for the comparative process (see FIG. 7). At constant $C_5+$ yields by weight as a percentage of $C_5+$ material in the reactor feed, conversion to 2,2-dimethylbutane is actually lower than for the comparative process (see FIG. 8). However, the activity advantage for total isohexane production is surprisingly greater than that for isopentane production, resulting in an isomerate product with an equivalent product RON and $C_5+$ yield at about a 50° F. lower reactor temperature than the comparative catalyst (see FIG. 9). As a result, selectivity for conversion of normal hexane to isohexane is higher for the process of the present invention than the comparative invention (see FIG. 10). The net result is that the present process produces more branched hexane isomers but less 2,2-dimethylbutane. These effects approximately offset, yielding similar octane selectivity results. However, the process of the present invention achieves these results at about a 40° F. to about 50° F. lower reaction temperature.

Figure 11:
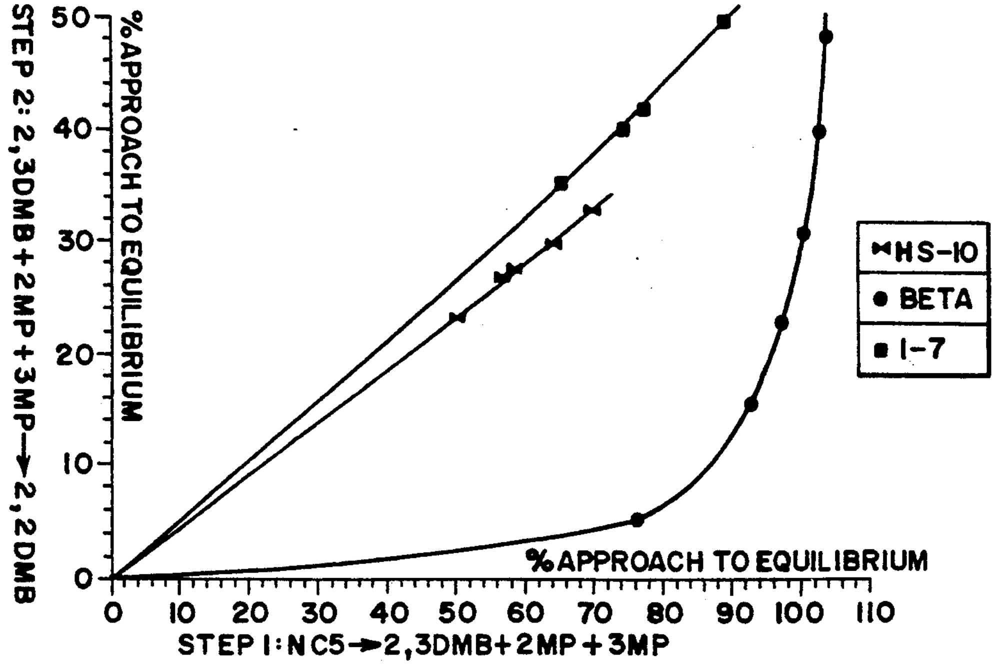
FIG. 11 is a graph illustrating a comparison of the performance of the catalyst of the present invention and two commercially available catalysts (UOP 1-7 and Union Carbide Hysomer) relative to the two steps of the hexane isomerization reaction.

FIG. 11 illustrates the performance of the zeolite beta catalyst of the present invention relative to the two reaction steps described above. For comparison, data for Union Carbide's HS-10 (Hysomer) catalyst and UOP's 1-7 catalyst are also illustrated on the same figure. The 1-7 and HS-10 catalysts behave similarly, although 1-7 is more active and displays some selective enhancement in the second step relative to HS-10. The activity of the zeolite beta catalyst of the present invention is much greater than 1-7, however the activity enhancement is asymmetric, pushing the first step essentially to equilibrium and with a smaller increase in the second step.

The process of the present invention results in a higher severity operation and in a higher octane isomerate product when operated at similar conditions to those of the comparative process. However, hydrocracking can be increased at these more severe conditions. Hydrocracking of light paraffinic naphtha to lower value products such as propane and butane and the lower resultant gasoline yield must be balanced against the incentives for higher octane isomerate. The penalties for higher severity isomerization and resultant hydrocracking are more severe during the summer months when tighter gasoline volatility specifications mandate removal of butane from gasoline. Higher reaction temperature operation also increases the catalyst deactivation rate resulting in costly facility downtime for catalyst regeneration or replacement. While the process of the present invention provides the capability of producing a higher octane isomerate product at similar reaction temperature to the comparative process, the penalties associated with hydrocracking and catalyst life can outweigh the benefits of higher octane operation. Therefore, the process of the present invention is best practiced when hydrocracking, defined as the conversion of hydrocarbon having 5 carbon atoms or more to hydrocarbon having 4 carbon atoms or less as a percentage of isomerization reactor feed having 5 carbon atoms or more by weight, is maintained at below about 10%, preferably below about 8%, and most preferably below about 6%. Light ends such as butane and propane that are produced through hydrocracking can remain in the isomerate product or be fractionated from the isomerate product and directed to other refinery or petrochemical processes, sold, fueled, or otherwise disposed of.

The isomerization process of the present invention achieves all of the advantages of high temperature processes featuring resilient and durable molecular sieve catalysts while providing a higher activity catalyst for higher octane operation or equivalent operation at a 40° F. to 50° F. lower reaction temperature. The process can operate under higher octane operation than comparative processes before reaching the point where the penalties of excessive hydrocracking outweigh the octane benefits. The process can operate at lower and more energy efficient reaction temperatures, at higher reactor space velocity (e.g., higher throughput), can process a more paraffinic lower octane feedstock, and/or be loaded with less catalyst while producing yields of higher octane isomerate equivalent to the comparative process.

The present invention is described in further detail in connection with the following examples, it being understood that the same are for purposes of illustration only and not limitation.

EXAMPLE 1

The present example describes the method of preparation for the catalyst utilized in the invention, light paraffin isomerization process.

A zeolite beta catalyst was synthesized having a silica to alumina ratio of about 20:1 by preparing a mixture containing tetraethylammonium hydroxide, water, sodium aluminate (Nalco 680), and colloidal silica (Ludox HS-40). The solution was crystallized at 302° F. for 136 hrs and the crystallized zeolite beta was washed with water and filtered. The filtered crystallized zeolite beta was dried at 221° F. and calcined at 1022° F. for 6 hrs. The zeolite beta catalyst produced had a micropore volume of 0.19 cc/gm.

The above crystalline zeolite beta catalyst was ion-exchanged by mixing with ammonium nitrate and water, stirring, and filtering. The filtered catalyst was dried for 12 hrs at 482° F.

The ion-exchanged catalyst was extruded to 1/16-in diameter cylinders by grinding the ion-exchanged catalyst above to 20 mesh, adding 1 part of alumina (Catapal) for every 4 parts of ion-exchanged catalyst, adding water, and extruding the mixture through a 1/16-inch die plate. The extruded catalyst was dried at 250° F. for 48 hrs, calcined at 400° F. for 4 hrs, and calcined at 800° F. for 3 hrs.

The resulting 80% zeolite beta 20% alumina extruded support was then exchanged by contacting with a solution of $NH_4NO_3$, distilled water, and $Pt(NH_3)_4(NO_3)_2$ and allowing the mixture to stand at room temperature for 12 hrs. The liquid portion was decanted and the catalyst was dried for 12 hrs at 250° F. and calcined at 800° F. for 3 hrs.

EXAMPLE 2

The feedstock utilized in testing the processes of the present invention and the comparison processes was a light paraffinic feedstock, fractionated from crude. The feedstock composition is described in Table IV below. Table IV includes all data from Examples 2-12 and is the data source for FIGS. 2-11.

The feedstock of Example 2 and all isomerate product streams produced from both the process of the present invention and the comparison cases, Examples 3-12, were sampled in the vapor state and analyzed for composition by an on-line gas chromatograph which was equipped with a 25 m capillary column (0.53 mm ID, ˀ micron film of OV-101) and an FID detector. Analyses are reported as area percent. Research octane (RON) is calculated as a linear combination of component blending octanes (Table III) for the $C_5+$ product. Conversions to isopentane, isohexane, and 2,2-dimethylbutane are calculated as the percentage of isopentane in the total pentane aliphatics and the percentage of branched hexanes and 2,2-dimethylbutane in the total hexane aliphatics, respectively. Total $C_5+$ product is calculated as the sum of all components with boiling points equal to or higher than isopentane (this does not include neopentane).

Isomerization Performance Numbers (IPN) were calculated for each stream of Examples 2-12. While product octane is often used to assess process performance, this parameter is feed dependent (some feedstocks produce higher octane product than others when processed at the same conditions). The IPN term reduces the quality of feed effect on final isomerate product octane that are not measured and compensated for when measuring the performance of an isomerization process or catalyst using octane number. The IPN is calculated by weight as follows:

$$IPN \text{ (percent)} = \text{isopentane conversion} +$$

$$\text{Dimethylbutane conversion}(DMB) =$$

$$\frac{\text{isopentane} \times 100}{\Sigma\ C_5 \text{ paraffins}} + \frac{[2,2\text{-}DMB + 2,3\text{-}DMB] \times 100}{\Sigma\ C_6 \text{ paraffins}}$$

The isopentane conversion and the DMB conversion parameters are generally limited by thermodynamic equilibrium to a maximum of about 65%-80% and 30%-45%, respectively. The IPN parameter is limited by thermodynamic equilibrium to a maximum of 95%-125%.

IPN-Yield numbers were also calculated for each stream of Examples 2-12. This term accounts for the loss of yield effect as a result of operations at higher reaction temperatures and measures the ability of a catalyst or a process to achieve high IPN while maintaining high yields of $C_5$+ product by weight. The IPN-Yield number is calculated as follows:

$$\text{IPN-Yield (percent)} = \text{IPN} \times C_5+ \text{ yield by weight.}$$

IPN-Yield numbers can equal but cannot exceed the maximum IPN number, since at a 100% yield of $C_5$+ material, IPN-Yield would equal IPN. The isomerate product IPN-Yield is preferably maintained above 65% by weight and more preferably above 70% by weight for best results.

TABLE III

| Blending Octane Numbers Used To Calculate RON | |
|---|---|
| Component | Blending Octane |
| i-pentane | 93.0 |
| n-pentane | 61.7 |
| 2,2-dimethylbutane | 91.8 |
| 2,3-dimethylbutane | 104.3 |
| 2-methylpentane | 73.4 |
| 3-methylpentane | 74.5 |
| n-hexane | 24.8 |
| methylcyclopentane | 91.3 |
| benzene | 99.0 |
| cyclohexane | 83.0 |
| 2-methylhexane | 91.1 |
| 3-methylhexane | 52.0 |
| n-heptane | 0.0 |
| methylcyclohexane | 74.8 |
| toluene | 108.0 |

TABLE IV

| EXAMPLE | 2 | 3 | 4 | 5 | 6 | 7 | 8 | 9 | 10 | 11 | 12 |
|---|---|---|---|---|---|---|---|---|---|---|---|
| CATALYST | | I-7 | I-7 | I-7 | I-7 | ZEOLITE BETA | ZEOLITE BETA | ZEOLITE BETA | ZEOLITE BETA | ZEOLITE BETA | ZEOLITE BETA |
| TEMPERATURE, F. | | 504 | 519 | 494 | 504 | 504 | 495 | 484 | 474 | 464 | 443 |
| WHSV, 1/hr. | | 1.70 | 1.70 | 1.60 | 1.72 | 1.76 | 1.82 | 1.79 | 1.79 | 1.79 | 1.79 |
| H2 Flow, SCF/B | | 1594 | 1594 | 1694 | 1571 | 1618 | 1571 | 1594 | 1594 | 1594 | 1594 |
| pH2, psia | | 140 | 139 | 143 | 139 | 138 | 137 | 138 | 139 | 139 | 140 |
| pHC, psia | | 90 | 91 | 87 | 91 | 92 | 93 | 92 | 91 | 91 | 90 |
| Total pressure, psig | | 215 | 215 | 215 | 215 | 215 | 215 | 215 | 215 | 215 | 215 |
| C1 | 0.00 | 0.02 | 0.04 | 0.02 | 0.02 | 0.06 | 0.05 | 0.03 | 0.02 | 0.01 | 0.01 |
| C2 | 0.00 | 0.04 | 0.06 | 0.03 | 0.04 | 0.11 | 0.08 | 0.06 | 0.04 | 0.02 | 0.01 |
| C3 | 0.03 | 1.22 | 1.71 | 0.91 | 1.15 | 3.31 | 2.67 | 2.07 | 1.73 | 1.45 | 1.07 |
| iC4 | 0.26 | 3.09 | 4.18 | 2.47 | 2.99 | 8.32 | 6.75 | 5.22 | 4.29 | 3.42 | 2.36 |
| nC4 | 0.41 | 0.77 | 0.98 | 0.70 | 0.78 | 1.62 | 1.33 | 1.08 | 0.89 | 0.79 | 0.62 |
| 2,2-dm-C3 | 0.00 | 0.06 | 0.08 | 0.05 | 0.06 | 0.08 | 0.06 | 0.04 | 0.04 | 0.03 | 0.03 |
| iC5 | 7.36 | 15.35 | 17.15 | 13.85 | 15.05 | 21.40 | 20.68 | 19.36 | 17.55 | 15.87 | 12.47 |
| nC5 | 21.54 | 14.21 | 12.68 | 15.68 | 14.72 | 9.99 | 10.37 | 11.40 | 12.25 | 13.68 | 16.20 |
| 2,2-dm-C4 | 2.69 | 8.12 | 8.68 | 7.42 | 7.86 | 7.86 | 7.52 | 6.93 | 6.52 | 5.85 | 4.80 |
| 2,3-dm-C4 | 5.64 | 7.64 | 7.41 | 7.76 | 7.68 | 6.64 | 7.11 | 7.55 | 7.93 | 8.18 | 8.51 |
| 2-m-C5 | 21.38 | 18.46 | 18.01 | 18.67 | 18.48 | 17.33 | 18.20 | 18.98 | 19.76 | 20.31 | 21.00 |
| 3-M-C5 | 13.68 | 11.94 | 11.74 | 12.02 | 11.94 | 11.24 | 11.76 | 12.18 | 12.64 | 12.88 | 13.16 |
| nC6 | 16.14 | 11.60 | 11.00 | 12.20 | 11.76 | 9.51 | 9.92 | 10.30 | 10.73 | 11.07 | 12.03 |
| m-cy-C5 | 5.25 | 4.50 | 3.73 | 4.93 | 4.52 | 1.22 | 1.79 | 2.54 | 3.17 | 3.84 | 4.69 |
| Benzene | 2.24 | 0.00 | 0.00 | 0.00 | 0.00 | 0.00 | 0.00 | 0.00 | 0.00 | 0.00 | 0.00 |
| cy-C6 | 0.67 | 1.30 | 1.02 | 1.48 | 1.30 | 0.34 | 0.53 | 0.81 | 1.06 | 1.34 | 1.81 |
| 2-m-C6 | 0.81 | 0.24 | 0.15 | 0.34 | 0.25 | 0.03 | 0.04 | 0.05 | 0.05 | 0.06 | 0.13 |
| 3-m-C6 | 0.67 | 0.20 | 0.13 | 0.28 | 0.21 | 0.03 | 0.03 | 0.04 | 0.04 | 0.05 | 0.12 |
| nC7 | 0.44 | 0.12 | 0.07 | 0.17 | 0.13 | 0.01 | 0.02 | 0.03 | 0.02 | 0.02 | 0.06 |
| m-cy-C6 | 0.05 | 0.43 | 0.47 | 0.37 | 0.40 | 0.40 | 0.49 | 0.55 | 0.55 | 0.48 | 0.39 |
| Toluene | 0.23 | 0.00 | 0.00 | 0.00 | 0.00 | 0.00 | 0.00 | 0.00 | 0.00 | 0.00 | 0.00 |
| Unidentified | 0.49 | 0.71 | 0.74 | 0.65 | 0.67 | 0.53 | 0.64 | 0.81 | 0.73 | 0.65 | 0.55 |
| C1-C4 | 0.70 | 5.20 | 7.04 | 4.17 | 5.04 | 13.49 | 10.94 | 8.49 | 7.01 | 5.73 | 4.10 |
| C5-C6 | 96.60 | 93.11 | 91.40 | 94.01 | 93.30 | 85.51 | 87.85 | 90.03 | 91.62 | 93.01 | 94.66 |
| C7+ | 2.70 | 1.69 | 1.56 | 1.81 | 1.66 | 1.00 | 1.21 | 1.48 | 1.38 | 1.26 | 1.25 |
| RON | 68.14 | 73.98 | 74.78 | 73.14 | 73.72 | 76.04 | 75.77 | 75.29 | 74.75 | 74.13 | 72.70 |
| iC5/total C5 paraffins, % | 25.48 | 51.93 | 57.50 | 46.90 | 50.55 | 68.18 | 66.61 | 62.93 | 58.90 | 53.70 | 43.49 |
| iC6/total C6 paraffins, % | 72.89 | 79.92 | 80.65 | 78.99 | 79.62 | 81.91 | 81.80 | 81.59 | 81.36 | 81.01 | 79.77 |
| 2,2-DMB/total C6 paraffins, % | 4.52 | 14.05 | 15.27 | 12.78 | 13.61 | 14.94 | 13.79 | 12.39 | 11.32 | 10.03 | 8.07 |
| IPN | | 79.2 | 85.8 | 73.0 | 77.5 | 95.8 | 93.4 | 88.8 | 84.0 | 77.8 | 65.9 |

TABLE IV-continued

| EXAMPLE | 2 | 3 | 4 | 5 | 6 | 7 | 8 | 9 | 10 | 11 | 12 |
|---|---|---|---|---|---|---|---|---|---|---|---|
| CATALYST | | I-7 | I-7 | I-7 | I-7 | ZEOLITE BETA | ZEOLITE BETA | ZEOLITE BETA | ZEOLITE BETA | ZEOLITE BETA | ZEOLITE BETA |
| IPN-Yield | | 75.1 | 79.8 | 70.0 | 73.6 | 82.8 | 83.2 | 81.3 | 79.1 | 73.3 | 63.2 |

Note:
The data from Examples 2 through 12 were utilized to develop FIGS. 2 through 11.

EXAMPLE 3

The feedstock of Example 2 was processed with a commercially available UOP 1-7 isomerization catalyst in a fixed-bed pilot plant. Hydrogen and the hydrocarbon feedstock of Example 2 were mixed in a heated transfer line and introduced into the top of the reactor, which was held in a molten salt bath. The reaction mixture passed downflow through a 30 ml bed of the UOP 1-7 catalyst (20/40 mesh). The reactor effluent lines were heated to about 500° F. Total reactor effluent was sampled periodically and analyzed by the on-line gas chromatograph described in Example 2.

The operating conditions consisted of an isomerization reaction temperature of 504° F., a space velocity (WHSV) of 1.70 $hr^{-1}$, a hydrogen addition rate of 1594 SCF/Bbl, and a reactor pressure of 215 psig. The process variables, gas chromatograph results, the isomerate research octane (RON), and the isomerate IPN and IPN-Yield numbers are listed in Table IV.

EXAMPLE 4

The feedstock of Example 2 was subjected to the same operating conditions as Example 3 but for an increase in isomerization reaction temperature from 504° F. to 519° F. The results are displayed in Table IV.

The IPN increased to 85.5% by weight and the IPN-Yield increased to 79.8% by weight as a result of the higher isomerization reaction temperatures.

EXAMPLE 5

The feedstock of Example 2 was subjected to the same operating conditions as Example 3 but for a decrease in isomerization reaction temperature from 504° F. to 494° F., a reduction in WHSV ($hr^{-1}$) from 1.70 to 1.60, and an increase in hydrogen addition rate of from 1594 SCF/Bbl to 1694 SCF/Bbl. The results are displayed in Table IV.

The IPN decreased to 73.0% by weight and the IPN-Yield decreased to 70.0% by weight as a result of the lower isomerization reaction temperature.

EXAMPLE 6

The feedstock of Example 2 was subjected to the same operating conditions as Example 3 but for a reduction in hydrogen addition rate from 1594 SCF/Bbl to 1571 SCF/Bbl and an increase in WHSV ($hr^{-1}$) of from 1.70 to 1.72. The results are displayed in Table IV.

The IPN decreased slightly to 77.5% by weight, and the IPN-Yield decreased slightly to 73.6% by weight due to the effects of the changes in the above process variables.

EXAMPLE 7

The feedstock of Example 2 was processed over the zeolite beta catalyst of the present invention described in Example 1.

The operating conditions of Example 7 are similar to the operating conditions with the UOP 1-7 catalyst set forth in Example 3 but for a slightly higher WHSV ($hr^{-1}$) of 1.76 as compared to 1.70 and a slightly higher hydrogen addition rate of 1618 SCF/Bbl as compared to 1594 SCF/Bbl. The results are displayed in Table IV.

Comparing the zeolite beta catalyst of Example 7 to the UOP 1-7 catalyst of Example 3, the IPN is increased substantially with the zeolite beta catalyst when used with the feedstock in accordance with the present invention, from 79.2% by weight to 95.8% by weight. The IPN-Yield is increased substantially from 75.1% by weight to 82.8% by weight.

EXAMPLE 8

The feedstock of Example 2 was subjected to the same operating conditions as Example 7 but for a reduction in isomerization reaction temperature of from 504° F. to 495° F., an increase in WHSV ($hr^{-1}$) of from 1.76 to 1.82, and a reduction in hydrogen addition rate of from 1618 SCF/Bbl to 1571 SCF/Bbl. The operating conditions of Example 8 are similar to the operating conditions with the UOP 1-7 catalyst displayed in Example 5 but for a higher WHSV ($hr^{-1}$) of 1.82 as compared to 1.60 and a lower hydrogen addition rate of 1571 SCF/Bbl as compared to 1694 SCF/Bbl. The results are displayed in Table IV.

Comparison of the two zeolite beta catalyst examples (Examples 7 and 8) shows that the IPN decreased from 95.8% by weight to 93.4% by weight while the IPN-Yield actually increased from 82.8% by weight to 83.2% by weight. This comparison illustrates that the lower reaction temperature operation may be preferred in this instance since the $C_5+$ yield benefits of lower reaction temperature operation can compensate for the actual IPN penalty.

Comparing the zeolite beta catalyst of Example 8 to the UOP 1-7 catalyst of Example 5, the IPN is increased substantially with the zeolite beta catalyst when used with the feedstock in accordance with the present invention, from 73.0% by weight to 93.4% by weight. The IPN-Yield is also increased substantially from 70.0% by weight to 83.2% by weight.

EXAMPLE 9

The feedstock of Example 2 was subjected to the same operating conditions as Example 7 but for a 20° F. reduction in isomerization reaction temperature of from 504° F. to 484° F. and a slight reduction in hydrogen addition rate of from 1618 SCF/Bbl to 1594 SCF/Bbl. The operating conditions of Example 9 are less severe than with the UOP 1-7 catalyst displayed in Example 5, including a lower reaction temperature of 484° F. as compared to 494° F., a higher WHSV ($hr^{-1}$) of 1.79 as compared to 1.60, and a lower hydrogen addition rate of 1594 SCF/Bbl as compared to 1694 SCF/Bbl. The results are displayed in Table IV.

Comparison of the two zeolite beta catalyst examples (Examples 7 and 9) shows that the IPN decreased from 95.8% by weight to 88.8% by weight while the IPN-Yield decreased slightly from 82.8% by weight to 81.3% by weight. This comparison illustrates that the lower reaction temperature operation in this instance is less preferred because the $C_5+$ yield benefits of lower reaction temperature are dominated by the lower IPN, resulting in a lower IPN-Yield.

Comparing the zeolite beta catalyst of Example 9 to the UOP 1-7 catalyst of Example 5 (despite the 10° F. higher reaction temperature of Example 5), the IPN of the zeolite beta catalyst when used in accordance with the present invention is substantially higher at 88.8% by weight as compared to 73.0% by weight. The IPN-Yield is also substantially higher for the zeolite beta catalyst of the present invention at 81.3% by weight as compared to 70.0%.

EXAMPLE 10

The feedstock of Example 2 was subjected to the same operating conditions as Example 7 but for a 30° F. reduction in isomerization reaction temperature of from 504° F. to 474° F. and a slight reduction in hydrogen addition rate of from 1694 SCF/Bbl to 1594 SCF/Bbl. The operating conditions of Example 10 are much less severe than with the UOP 1-7 catalyst displayed in Example 5, including a lower reaction temperature of 474° F. as compared to 494° F., a higher WHSV ($hr^{-1}$) of 1.79 as compared to 1.60, and a lower hydrogen addition rate of 1594 SCF/Bbl as compared to 1694 SCF/Bbl. The results are displayed in Table IV.

Comparison of the two zeolite beta catalyst examples (Examples 7 and 10) shows that the IPN decreased from 95.8% by weight to 84.0% by weight while the IPN-Yield decreased from 82.8% by weight to 78.1% by weight. This comparison illustrates that the lower reaction temperature operation of Example 10 is less preferred than the operation of Example 7 because the $C_5+$ yield benefits of lower reaction temperature are dominated by the lower IPN, resulting in a lower IPN-Yield.

Comparing the zeolite beta catalyst of Example 10 to the UOP 1-7 catalyst of Example 5 (despite the 20° F. higher reaction temperature of Example 5), the IPN of the zeolite beta catalyst when used with the feedstock in accordance with the present invention is substantially higher at 84.0% by weight as compared to 73.0% by weight. The IPN-Yield is also substantially higher at 78.1% by weight as compared to 70.0% by weight.

EXAMPLE 11

The feedstock of Example 2 was subjected to the same operating conditions as Example 7 but for a 40° F. reduction in isomerization reaction temperature from 504° F. to 464° F. and a slight reduction in hydrogen addition rate of from 1694 SCF/Bbl to 1594 SCF/Bbl. The operating conditions of Example 11 are much less severe than with the UOP 1-7 catalyst displayed in Example 5, including a lower reaction temperature of 464° F. as compared to 494° F., a higher WHSV ($hr^{-1}$) of 1.79 as compared to 1.60, and a lower hydrogen addition rate of 1594 SCF/Bbl as compared to 1694 SCF/Bbl. The results are displayed in Table IV.

Comparison of the two zeolite beta catalyst examples (Examples 7 and 11) shows that the IPN decreased from 95.8% by weight to 77.8% by weight while the IPN-Yield decreased from 82.8% by weight to 73.3% by weight. This comparison illustrates that the lower reaction temperature operation is less preferred than the operation of Example 7 because the $C_5+$ yield benefits of lower reaction temperature operation are dominated by the lower IPN, resulting in a lower IPN-Yield.

Comparing the zeolite beta catalyst of Example 11 to the UOP 1-7 catalyst of Example 5 (despite the 30° F. higher reaction temperature of Example 5), the IPN of the zeolite beta catalyst when used with the feedstock in accordance with the present invention remains higher than the UOP 1-7 catalyst process of Example 5 at 77.8% by weight as compared to 73.0% by weight. The IPN-Yield also remains higher at 73.3% by weight as compared to 70.0% by weight.

EXAMPLE 12

The feedstock of Example 2 was subjected to the same operating conditions as Example 7 but for a 61° F. reduction in isomerization reaction temperature of from 504° F. to 443° F. and a slight reduction in hydrogen addition rate of from 1694 SCF/Bbl to 1594 SCF/Bbl. The operating conditions of Example 12 are much less severe than with the UOP 1-7 catalyst displayed in Example 5, including a lower reaction temperature of 443° F. as compared to 494° F., a higher WHSV ($hr^{-1}$) of 1.79 as compared to 1.60, and a lower hydrogen addition rate of 1594 SCF/Bbl as compared to 1694 SCF/Bbl. The results are displayed in Table IV.

Comparison of the two zeolite beta catalyst examples (Examples 7 and 12) shows that the IPN decreased from 95.8% by weight to 65.9% by weight while the IPN-Yield decreased from 82.8% by weight to 63.2% by weight. This comparison illustrates that this lower reaction temperature operation is less preferred than the operation of Example 7 because the $C_5+$ yield benefits of lower reaction temperature operation are dominated by the lower IPN, resulting in a lower IPN-Yield.

Comparing the zeolite beta catalyst of Example 12 to the UOP 1-7 catalyst of Example 5 (at the 51° F. higher reaction temperature of Example 5), the IPN of the zeolite beta catalyst of the present invention finally falls below that of the process using the UOP 1-7 catalyst at 65.9% by weight as compared to 73.0% by weight. The IPN-Yield is also lower at 63.2% by weight as compared to 70.0% by weight. The examples above illustrate that the present inventive process utilizing zeolite beta catalyst achieves far superior performance than the UOP 1-7 catalytic process at less than about a 40° F. reduction in isomerization reaction temperature or equivalent performance at about a 40° F. lower reaction temperature.

That which is claimed is:

1. A process for the isomerization of a light paraffinic hydrocarbon feedstock, said feedstock comprising a stream having a boiling range of from about 50° F. to about 210° F. and at least 85 weight percent aliphatic hydrocarbon having 6 carbon atoms or less, wherein said process comprises contacting said feedstock at isomerization conditions comprising an operating temperature of not more than about 520° F., with an isomerization catalyst comprising a zeolite beta component and producing an isomerate product having an isopentane to total pentane concentration percentage by weight of not less than about 54 percent and containing less than about 8 percent by weight of hydrocarbon having less than 5 carbon atoms produced through hydrocracking.

2. The process of claim 1 wherein said feedstock comprises a stream having a boiling range of from about 50° F. to about 210° F. and contains less than about 10 weight percent cyclic hydrocarbon plus noncyclic hydrocarbon with 7 or more carbon atoms.

3. The process of claim 1 wherein said isomerization catalyst comprises from about 95 to about 99.99 percent by weight of a support component, said support component comprising from about 10 to about 99 percent by weight of a zeolite beta component and from about 1 to about 90 percent by weight of a binder component, and from about 0.01 percent to about 5 percent by weight on an elemental basis of a metal component selected from the Group VIII elements of the Periodic Table.

4. The process of claim 3 wherein said isomerization catalyst comprises a zeolite beta component with a $SiO_2$:$Al_2O_3$ molar ratio of between about 4:1 to about 100:1.

5. The process of claim 1 wherein said feedstock comprises at least 91 weight percent aliphatic hydrocarbon having 6 carbon atoms or less.

6. The process of claim 1 wherein said feedstock comprises less than 3 weight percent butane.

7. The process of claim 1 wherein said feedstock comprises less than 3 ppm by weight of sulfur and less than 3 ppm by weight of nitrogen.

8. The process of claim 1 wherein said isomerization conditions comprise an operating temperature of from about 300° F. to about 520° F., an operating pressure of from about 100 psig to about 600 psig, and a space velocity of from about 0.1 to about 10.0 WHSV ($hr^{-1}$).

9. A process for the isomerization of a light hydrocarbon feedstock comprising at least 85 weight percent aliphatic hydrocarbons having 5 to 6 carbon atoms and less than 10 weight percent cyclic hydrocarbon plus non-cyclic hydrocarbons having at least 7 carbon atoms, wherein said process comprises contacting said feedstock at isomerization conditions comprising an operating temperature of not more than about 520° F. with an isomerization catalyst comprising a Group VIII hydrogenation metal and from about 95 percent to about 99.9 percent by weight of a support component comprising zeolite beta and producing an isomerate product having an isopentane to total pentane concentration percentage by weight of not less than about 54 percent and containing less than 8 percent by weight of hydrocarbon having less than 5 carbon atoms produced through hydrocracking.

10. The process of claim 9 wherein said isomerization catalyst comprises from about 99 percent to about 99.9 percent by weight of a support component, said support component comprising from about 40 to about 99 percent by weight of a zeolite beta component and from about 1 to about 60 percent by weight of a binder material, and from about 0.1 percent to about 1 percent by weight on an elemental basis of a metal component selected from the group consisting of platinum and palladium.

11. The process of claim 10 wherein said isomerization catalyst comprises a zeolite beta component with a $SiO_2$/$Al_2O_3$ molar ratio of between about 6:1 to about 50:1.

12. The process of claim 9 wherein said feedstock comprises less than 2 ppm by weight of sulfur and less than 2 ppm by weight of nitrogen.

13. The process of claim 12 wherein said feedstock sulfur and nitrogen levels are attained by hydrotreating.

14. The process of claim 9 wherein said feedstock comprises less than 2 percent by weight of butane.

15. The process of claim 9 wherein said isomerization conditions comprise an operating temperature of from about 400° F. to about 520° F., an operating pressure of from about 200 psig to about 400 psig, and a space velocity of from about 0.5 to about 5.0 WHSV ($hr^{-1}$).

16. The process of claim 9 wherein said isomerization conditions comprise a hydrogen circulation rate of from about 200 SCF/Bbl of isomerization reactor feedstock to about 2000 SCF/Bbl of isomerization reactor feedstock.

17. The process of claim 9 wherein said isomerization process operates at an Isomerization Performance Number-Yield of at least 65 percent by weight.

18. A process for the isomerization of a light paraffinic hydrocarbon feedstock comprising at least 85 weight percent aliphatic hydrocarbon having 5 to 6 carbon atoms and less than 10 weight percent cyclic hydrocarbon plus non-cyclic hydrocarbon having at least 7 carbon atoms, wherein said process comprises contacting said feedstock with an isomerization catalyst comprising from about 99 to about 99.9 percent by weight of a support component, said support component comprising from about 60 percent to about 90 percent by weight of a zeolite beta component, and from about 0.1 to about 1 percent by weight of platinum on an elemental basis at isomerization conditions wherein said conditions include a reaction temperature of from about 400° F. to about 520° F. and a reaction pressure of from about 200 psig to about 400 psig and producing an isomerate product having an isopentane to total pentane concentration percentage by weight of not less than about 54 percent and containing less than 8 percent by weight of hydrocarbon having less than 5 carbon atoms produced through hydrocracking.

19. The process of claim 18 wherein said isomerization catalyst comprises from about 99.2 to about 99.8 percent by weight of a support component, said support component comprising from about 70 to about 80 percent by weight of a zeolite beta component and from about 20 to about 30 percent by weight of an alumina binder, and from about 0.2 percent to about 0.8 percent by weight on an elemental basis platinum.

20. The process of claim 19 wherein said isomerization catalyst comprises a zeolite beta component with a $SiO_2$:$Al_2O_3$ molar ratio of between about 8:1 and about 30:1.

21. The process of claim 18 wherein said feedstock comprises less than 2 ppm by weight of sulfur and less than 2 ppm by weight of nitrogen.

22. The process of claim 21 wherein said feedstock sulfur and nitrogen levels are attained by hydrotreating.

23. The process of claim 18 wherein said feedstock comprises less than 2 percent by weight butane.

24. The process of claim 18 wherein said isomerization conditions comprise an operating temperature of from about 450° F. to about 500° F., and operating pressure of from about 250 psig to about 350 psig, and a space velocity of from about 1.0 to about 3.0 WHSV ($hr^{-1}$).

25. The process of claim 18 wherein said isomerization conditions comprise a hydrogen circulation rate of from about 500 SCF/Bbl of isomerization reactor feedstock.

26. The process of claim 18 wherein said isomerization process operates at an Isomerization Performance Number-Yield of at least 70 percent by weight.

* * * * *